United States Patent
Cramer et al.

(10) Patent No.: US 7,329,222 B2
(45) Date of Patent: Feb. 12, 2008

(54) COMPARATIVE FIELD ANALYSIS (COMFA) UTILIZING TOPOMERIC ALIGNMENT OF MOLECULAR FRAGMENTS

(75) Inventors: Richard D. Cramer, Sante Fe, NM (US); Robert Jilek, St. Peters, MO (US)

(73) Assignee: Tripos, L.P., San Francisco, CA (US)

( * ) Notice: Subject to any disclaimer, the term of this patent is extended or adjusted under 35 U.S.C. 154(b) by 0 days.

(21) Appl. No.: 10/374,741

(22) Filed: Feb. 25, 2003

(65) Prior Publication Data

US 2003/0236631 A1 Dec. 25, 2003

Related U.S. Application Data

(60) Provisional application No. 60/359,947, filed on Feb. 25, 2002.

(51) Int. Cl.
  *C40B 30/02* (2006.01)
  *G06F 19/00* (2006.01)
  *G01N 31/00* (2006.01)

(52) U.S. Cl. .............................. 506/8; 702/19; 702/22; 702/27; 702/152; 702/153.1

(58) Field of Classification Search ................ 702/19, 702/22, 27, 152, 153, 1
  See application file for complete search history.

(56) References Cited

U.S. PATENT DOCUMENTS 6,185,506 B1 * 2/2001 Cramer et al. ................ 702/19

* cited by examiner

*Primary Examiner*—Lori A. Clow
(74) *Attorney, Agent, or Firm*—Laurence Weinberger

(57) ABSTRACT

The static and electrostatic interaction energy fields between probe atoms and the atoms of a topomerically aligned fragment placed in a three-dimensional grid may be used to derive a CoMFA model. The topomeric CoMFA model coefficients may be used to predict partial activity values for fragments not derived from molecules of the activity series. The partial activities can be summed to provide a predicted activity for all fragment positions of the activity series molecules. A Virtual Library in which topomerically aligned fragments are associated with their respective steric and electrostatic interaction energies can be searched for fragments similar in shape to the fragments derived from the molecules of the activity series. The identified fragments can be used with the topomeric CoMFA coefficients to predict their activity if used in the molecular activity series.

4 Claims, 9 Drawing Sheets

FIG. 7

Table 1

| Dataset Name | Ref # | Biological activity | Structural class | Literature CoMFA methods | | | Topomer CoMFA | | Common Core or Fragmentation Bond |
|---|---|---|---|---|---|---|---|---|---|
| | | | | Conformer | Orient | PLS[a] | Omit IDs | Frag Case | |
| ICEc | | Interleukin 1-b converting enzyme inhibitor | doubly blocked mono- to tripeptides | docking to enzyme 1ICE; mutation; minimization | RMS fit to backbone atoms | A | 17,30 T1[b] | 1 | |
| ICEb | | | | | | | none | 2 | |
| thrombin | | inhibition of thrombin | N-sulfonylated-C-amino derivatives of 3-amidino-phenylalanine | docking into 1ETS, 1PPH, 1HCG; systematic search; minimization | | A | none | 1 | |
| trypsin | | inhibition of trypsin | | | | | | | |
| factorXa | | inhibition of Factor Xa | | | | | | | |
| MAOa | | inhibition of MAO-A | mostly 7-benzyloxy-coumarins | coumarins only; minimization of "flat" conformer | RMS fit to coumarin ring | B | all 71 used (lit. used < 45)[f] | 2 | |
| MAOb | | inhibition of MAO-B | | | | | | | |
| hiv | | inhibition of HIV-1 Protease | derivatives of cyclic sulfamides | crystal structure; dock with fixed core; Monte Carlo minimization of side chains (all 2048 asymmetry combinations examined with standard CoMFA including parabolic fields) | | | none | 1 | |
| a2a | | $A_{2A}$ adenosine receptor agonists | adenosine derivatives | substituents added to X-ray structure of adenosine | RMS fit to N3, C6, N7, N9 of purine ring | A | 113[c] | 1 | |
| d4 | | D4 receptor antagonism | heterocyclic-CH2-piperazines | substituents added to a clozapine-inspired core, some minimized | "field-fit" using ASP | A | none | 2 | |
| flav | | binding to benzodiazepine site in $GABA_A$ receptors | flavonoids | lowest energy conformer (systematic search, minimization) | RMS fit to aryl ring centroids and carbonyl O | A | none | 2 | |

FIG. 7 (continuation Table 1)

| | | | | | | | | |
|---|---|---|---|---|---|---|---|---|
| cannab | displacing WIN-55212-2 from CB₁ receptors | aminoalkyl-indoles | lowest energy conformer around C=O (systematic search, minimization) | RMS fit to indole N, carbonyl O, another C | A | none | 2 | 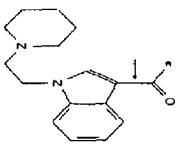 |
| ACest | inhibition of acetylcholin esterase from Torpedo californica | 4-phenylamino-pyridazines | docking into 1ACL, 2ACK, 1ACJ, 1VOT | | B | 6k[d] | 2 | 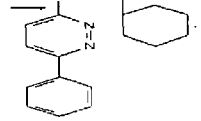 |
| 5ht3 | displacing 5-HT₃ from NG 108-15 cells | heterocyclic-piperazines | CATALYST hypothesis | | A | 19-23, 68-74[e] | 2 | 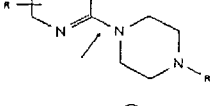 |
| rvtrans | protection of MT-4 cell from HIV-1 | thymines | minimization of ALCHEMY models with GAUSSIAN94 | RMS fit to thymine heavy atoms | A | none | 2 | 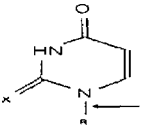 |

[a]A denotes the standard CoMFA method within SYBYL. B indicates use of GOLPE.
[b]These structures did not contain the common structure (Asp)
[c]Structure not given for this compound
[d]Structure not understood for this compound
[e]These structures would have been fragmented at a double bond, which topomerically is not yet defined.
[f]By including non-coumarin compounds, compounds which for solubility reasons did not reach 50% inhibition (logIC50 estimated by logit transform) and compounds showing no activity at the solubility limit (assigned an arbitrary low logIC50 value of 3.0).

FIG. 8

Table 2

|  | Lit. | Top1[a] | Top2[b] |
|---|---|---|---|
| Avg. # PLS Components | 4.2 | 5.5 | 3.6 |
| Avg $q^2$ (n=15) | .636 | .520 | .502 |
| Avg Sdev Prediction[c] (n=133) | .574 | .623 | .565 |

[a]Using standard CoMFA fields and methods
[b]Using "topomeric CoMFA fields". #comp from xval SDEV min, not $q^2$ max
[c]Omission of one data set having suspect predictions

COMPARATIVE FIELD ANALYSIS (COMFA) UTILIZING TOPOMERIC ALIGNMENT OF MOLECULAR FRAGMENTS

Benefit of U.S. Provisional Application No. 60/359,947 filed Feb. 25, 2002 is hereby claimed. A portion of the disclosure of this patent document contains material which is subject to copyright protection. The copyright owner has no objection to the facsimile reproduction by anyone of the patent document or the patent disclosure, as it appears in the U.S. Patent and Trademark Office but otherwise reserves all copyright rights whatsoever.

BACKGROUND

1. Field of the Invention

This invention relates generally to a method for performing the powerful CoMFA shape analysis methodology on certain classes of molecular structures, and, in particular, on molecular structures which may be decomposed/viewed as assemblies of discrete identifiable subunits such as those structures formed by combinatorial synthesis. In this invention, alignment of the molecular subunits for CoMFA analysis is achieved by a rule based procedure. The fields of the aligned subunits used in the CoMFA can be used to search a Virtual Library of precomputed fields for other subunits accessible in the chemical universe which have a similar shape and could be substituted as subunits in the molecular structures for which the CoMFA was derived. The likely activity for the molecules assembled using the subunits identified in the Virtual Library can be predicted using the CoMFA derived coefficients.

2. Description of Related Art

Since its introduction approximately a decade ago, Comparative Molecular Field Analysis (CoMFA) has become recognized[1] as a superior 3D-QSAR methodology. One recent reference[2] notes that from the years 1989 to 2000 over 5,000 publications are indexed using the keyword "CoMFA." A wide variety of problems in medicinal chemistry have been the subject of CoMFA modelling. CoMFA, like earlier 3D-QSAR approaches, represents a relevant measured molecular parameter for each molecule (typically biological affinity when used in medicinal chemistry) as a linear combination of descriptors which reflect the three dimensional molecular shape. Typically, several molecules in a series possessing similar activity, but differing in molecular share, are analyzed using CoMFA to determine those shape features associated with increased or decreased activity. Thus, CoMFA correlates the shapes of molecules with their (biological) activities. A full description of the CoMFA methodology is provided in U.S. Pat. No. 5,025,388 and U.S. Pat. No. 5,307,287.

In CoMFA, a quantitative description of the shape of a molecule is derived from the steric and electrostatic interaction energies between a test probe and each of the atoms comprising the molecule. Each molecule in the activity series is placed by the computer implemented methodology in a three dimensional lattice and the interaction energies determined as the probe is placed at all intersections of the lattice. The resulting interaction energies for each grid position are entered into column positions in a row of a data table associated with the measured parameter (activity) of each molecule. This procedure is repeated for all molecules in a series and is schematically illustrated in FIG. 1 of U.S. Pat. Nos. 5,025,388 and 5,307,287 which Figure is included in the present patent document as FIG. 1. After the data table is completed, Partial Least Squares (PLS) analysis using a cyclic cross-validation procedure is utilized to extract a set of coefficients for each column position (lattice point) that best reflects that position's contribution to the measured activity. The PLS procedure is schematically illustrated in FIG. 2 of U.S. Pat. Nos. 5,025,388 and 5,307,287 which Figure is included in the present patent document as FIG. 2.

An important consequence of the CoMFA method is that the likely activity of a molecule not included in the CoMFA model can be predicted using the column coefficients derived from the CoMFA analysis. The molecule of interest is aligned and positioned in the lattice, interaction energies are determined, and those interaction energies are placed in their respective columns. The predicted activity is then calculated by multiplying each interaction energy by the coefficients derived from the original CoMFA model data table:

$$V_{PREDICTED} = b + A_{001}S^1(001) + A_{002}S^1(002) + \ldots A_N S^1(N) + a_{001}E^1(001) + a_{002}E^1(002) + \ldots a_N E^1(N)$$

where $V_{PREDICTED}$ is the predicted activity for the proposed molecule; b is the intercept for the CoMFA model; $A\_$ and $a\_$ are the coefficients of the steric and electrostatic terms which reflect the relative contribution of each spatial location, the subscripts indicating both different coefficient values and the lattice positions with which the values are associated; $S^x(N)$ and $E^x(N)$ are the steric and electrostatic interaction energies calculated at lattice position N (where N ranges from 1 to the maximum number of lattice intersection points) determined for the proposed molecule.

It is important to note that CoMFA does not tell a chemist/user what alterations to the molecular structure to test. CoMFA only indicates those volumes around the known structures which are associated with increased or decreased activity. The chemist/user decides what changes to the molecular structure to try. The results of the CoMFA analysis (column coefficient values) can then be used to predict the likely activity for the shape of the molecule specified by the chemist/user.

As noted in the extensive discussion in the cited patents, the alignments of a series of molecules in the three dimensional lattice is critical to obtaining good results. Two aspects of the alignment are crucial. First, recognizing that even for the same molecule a slight shift in its position in the lattice will produce different interaction energies at different lattice locations, it is important that similar parts of similar molecules must be located at identical locations so as not to introduce meaningless differences. Second, it is important that, to the maximum extent possible, the major space occupying features of each molecule should be aligned with each other. In this manner the CoMFA methodology can distinguish the three dimensional features which are relevant to the observed activity. An extensive literature has grown up describing different alignment techniques to employ with the CoMFA methodology.

As combinatorial synthesis techniques were developed over the past few years to generate libraries of compounds which could be screened against different (primarily biological) targets, a similar alignment problem arose for those trying to design the libraries. Depending on the requirements, a library of similar compounds might be desired having similar activities in a specific assay or a library of dissimilar compounds might be desired which could be used to look for compounds which might have an activity in a chosen assay. The problem was how to choose the molecules before synthesis so that a great deal of time and money would not be wasted on synthesizing and assaying compounds which did not have a high probability of providing useful information. Over the years a variety of molecular structural metrics had been devised with which to characterize molecular structures. However, in the absence of any methodology which would indicate which, if any, of the metrics behaved as desired, use of the metrics to design libraries was not much better than a random selection process.

In U.S. Pat. No. 6,185,506 a method of validating molecular metrics is taught. The Patterson Plot methodology is based on the similarity principle which requires that any valid descriptor must have a neighborhood property; that is, the descriptor must meet the similarity principle's constraint that it measure the chemical universe in such a way that similar structures (as defined by the descriptor) have substantially similar properties (activities). This can also be stated to require that, within some radius in descriptor space of any given molecule possessing some property, there should be a high probability that other molecules found within that radius will also have the same property. Only descriptors which have the neighborhood property are "valid." Here "validity" is based on a high probability, not a certainty, that compounds similar in descriptor space will have similar activity. The Patterson Plot validation methodology can be applied to any molecular structural descriptor. As a consequence of the metric validation methodology, a "neighborhood radius" for each type of descriptor is defined.

In combinatorial syntheses, two or more reactants are combined to yield a product molecule. In the simplest case, reactant A and reactant B are joined by a common bond as in the molecule: A-B as shown in FIG. 3(a). In a slightly more complex case as shown in FIG. 3(e), reactant $R^1$ and reactant $R^2$ are joined by separate bonds to a common core or scaffold structure: $R^1$-CORE-$R^2$. In more complex cases as shown in FIG. 3(g), three or more reactants $R^1$, $R^2$, and $R^3$ may be individually bonded to a common core. For library design, a metric was needed which would validly characterize combinatorially derived molecules. A further problem which was presented was how to define a metric that could take into account the fact that reactants may assume many conformations both before and after chemical combination. The solution was to define a rule based procedure for aligning the reactants which was uniformly applied to every reactant. [As will be more fully described below, it is the fragments derived from reactants which are aligned by this procedure.] The particular rule base alignment procedure taught in U.S. Pat. No. 6,185,506 is referred to as the "topomeric" alignment. The procedure specifies a unique orientation in space as well as a similar conformation for each reactant. While the topomeric alignment of any given reactant may or may not resemble the conformation the reactant might naturally assume when binding to a receptor as part of a ligand, the topomeric generated conformation turned out to be a valid alignment approach.

In particular, when a metric is defined by the steric interaction fields around each topomerically aligned reactant fragment in a three dimensional lattice, the resulting metric was shown to be valid by the Patterson Plot methodology by application across a wide range of biological activities. Use of a metric consisting of the steric fields about topomerically aligned fragments enabled the computer implemented virtual design of molecular libraries having either similar structures or diverse structures. Use of this metric enabled an estimation of the similarity of combinatorially assembled molecules. Molecules with similar structures within the metric neighborhood radius should have similar biological properties. Molecules with structures outside the metric neighborhood radius should not have highly similar properties.

Initially, the metric consisting of the steric fields about topomerically aligned fragments was used to design libraries involving few starting reactants and cores. However, it was soon discovered that searches through vast chemical spaces of molecules which could be combinatorially assembled could be achieved. The construction and searching of such a vast library (referred to as the "Virtual Library") is taught in U.S. Pat. No. 6,240,374. Using metrics validated by the Patterson Plot methodology, it is possible to precompute the metric properties of the various component parts of molecules which could be combined in a combinatorial synthesis. A combination of the metric properties of the component parts yields a valid estimation of the properties of the resulting whole molecule. Potential combinatorially derived molecules can then be selected for similarity or dissimilarity before they are synthesized. At present the Virtual Library employed by the inventors contains precomputed metric data on sufficient component parts to characterize tens of trillions of possible combinatorially derivable molecules. The structure of the Virtual Library permits any characterizing data related to each component part to be associated with that part and searched for independently of any other data. For instance, in addition to the characterizing metric values, information on suppliers, cost, possible routes of synthesis for the molecules incorporating the component part, properties affecting bio-availability, etc. may all be associated with the component part in the Virtual Library by virtue of the manner of its construction.

One very important aspect of the characterization of the component parts of the Virtual Library with the metric consisting of the steric fields about topomerically aligned fragments is the ability to search through the vast chemical space of the Virtual Library to identify possible molecules which have a high probability of having the same activities as a molecule of interest. In addition, since the overall shape similarity (similarity in steric fields) is searched, it is possible that molecules arising from different chemistries may well be found to possess sufficiently similar shapes to display activity at the same target. In practice, searches of the Virtual Library for similarly shaped component parts, and molecules derived therefrom, amongst the trillions of molecules possible can be accomplished in relatively short time. Depending on where the cut-off level for identifying similarly shaped fragments is set, searches of a chemical space of billions of possibilities may take only a few hours.

The use of the metric consisting of the steric fields about topomerically aligned fragments has proven to be very fruitful in the design of combinatorial libraries and in searching a vast combinatorially accessible molecular structural universe. However, due to the inherently artificial structures generated by the rule based topomeric alignment procedure, further use outside the combinatorial design field has not been previously implemented. In particular, nothing in the prior art of CoMFA alignments suggests that such artificially rule based generated molecular shapes would be useful or valid in generating a CoMFA model.

DESCRIPTION OF FIGURES

FIG. 7 is a table of the literature sets used to compare standard CoMFA models to those generated by the topomeric CoMFA method of the present invention.

FIG. 8 is a table comparing the results of standard CoMFA and topomeric CoMFA QSAR models.

DETAILED DESCRIPTION OF THE INVENTION

Figure 1:
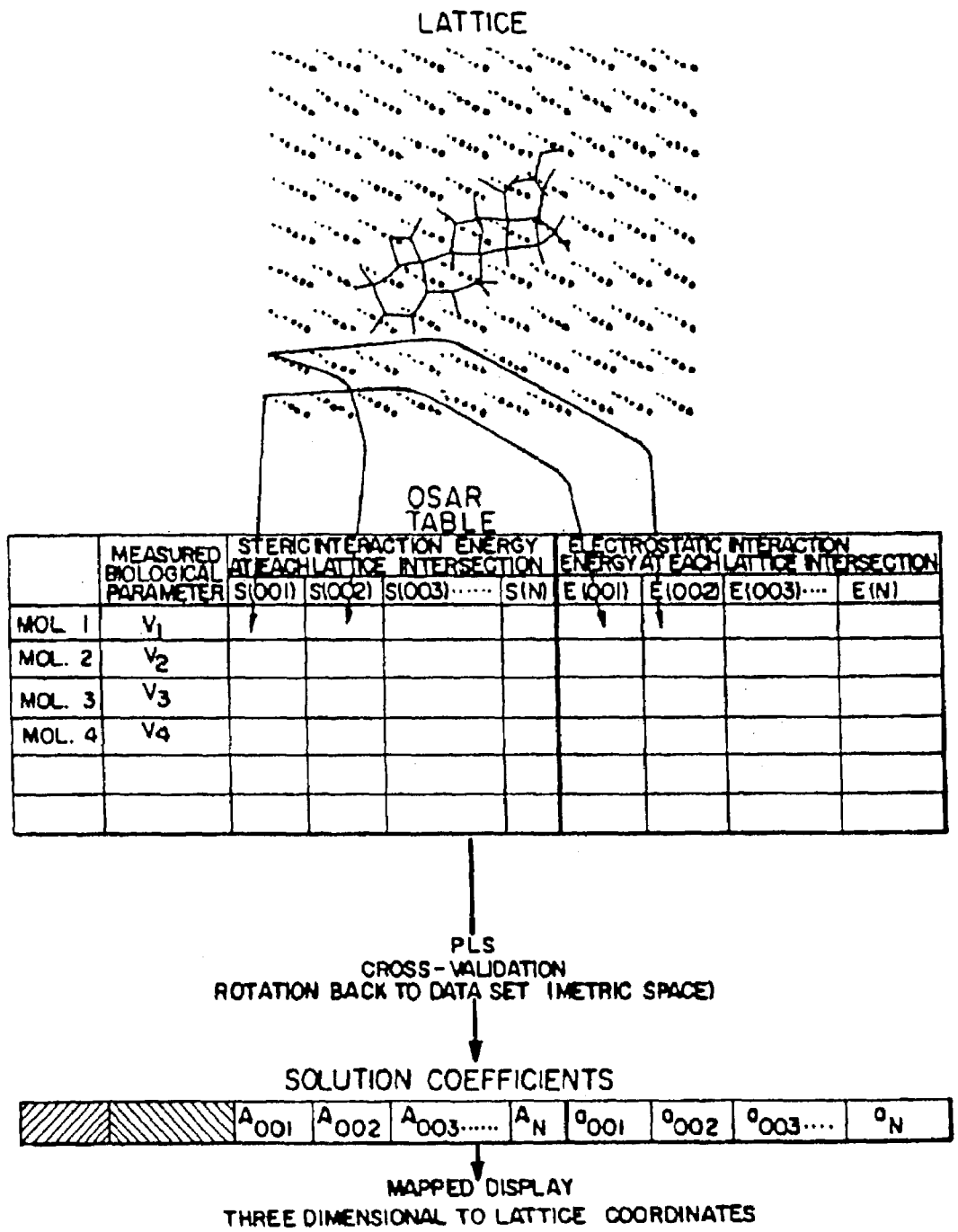
FIG. 1 is a schematic illustration and overview of the CoMFA method.
Figure 2:
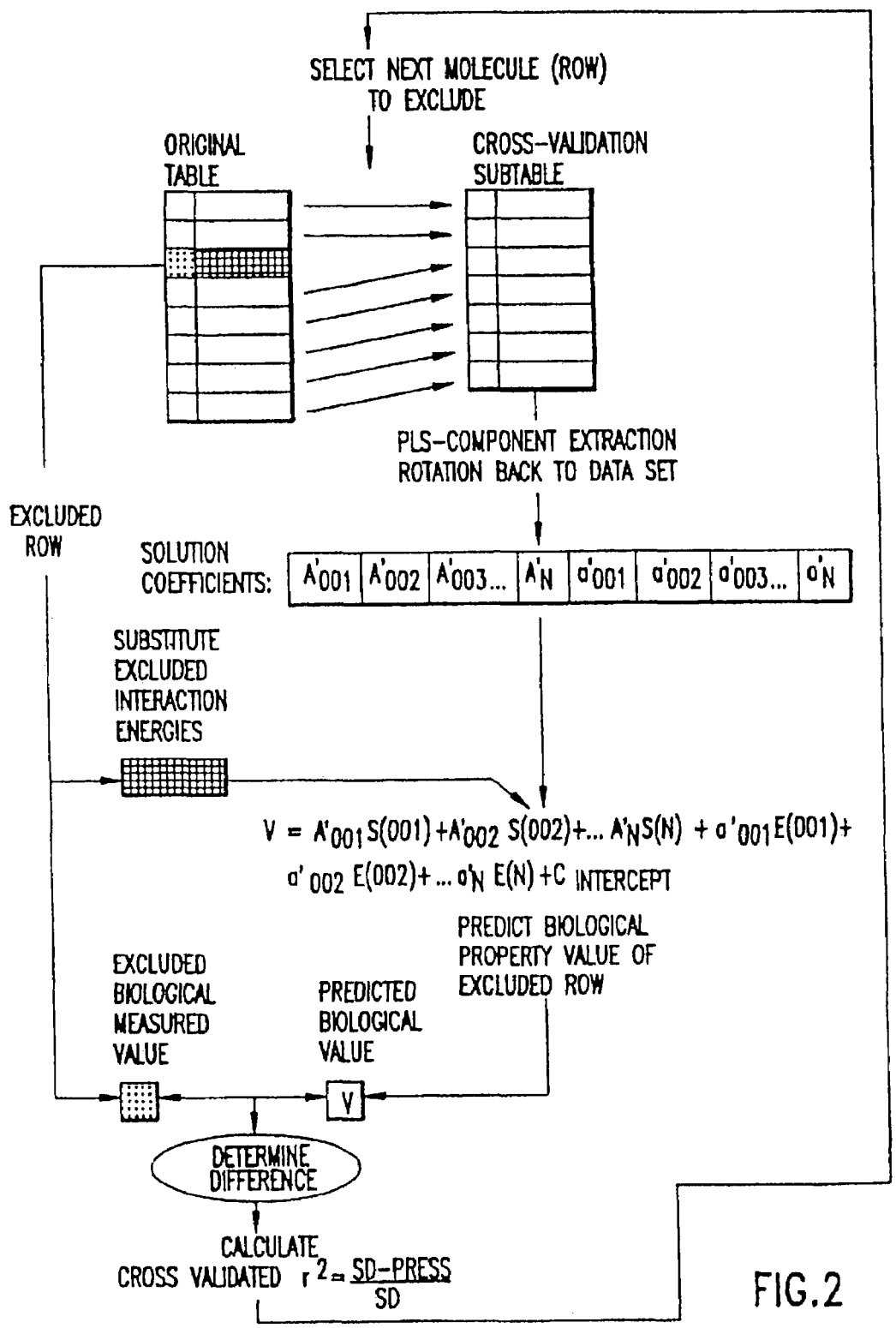
FIG. 2 is a schematic illustration and overview of the PLS method applied in CoMFA.

The "topomeric COMFA" methodology of the present invention starts with two major steps: 1) the generation of the topomer 3D models for each fragment and the generation of the interaction energy fields; and 2) the CoMFA analysis itself. Subsequent to the derivation of the topomeric CoMFA model, the steric metric fields derived for the topomeric fragments may be used to search a Virtual Library of component parts for fragments having similar three dimensional shapes (field values). The field values of the fragments identified in the Virtual Library can then be used with the topomeric CoMFA model derived coefficients to predict the likely activity of molecules assembled from the identified fragments.

A. Computational Chemistry Environment

Generally, all calculations and analyses to characterize fragments with valid metrics, perform topomeric CoMFA, search for similar molecular shapes in a Virtual Library of precomputed parts, and predict activities of possible molecules are implemented in a modern computational chemistry environment using software designed to handle molecular structures and associated properties and operations. For purposes of the present application, such an environment is specifically referenced. In particular, the computational environment and capabilities of the SYBYL and UNITY software programs developed and marketed by Tripos, Inc. (St. Louis, Mo.) are specifically utilized. Software with similar functionalities to SYBYL and UNITY are available from other sources, both commercial and non-commercial, well known to those in the art. Software to practice CoMFA may be commercially licensed from Tripos, Inc. as part of SYBYL. The required CoMFA software code was also disclosed as part of U.S. Pat. No. 5,025,388 and U.S. Pat. No. 5,307,287. For purposes of the present application, a reference to "standard CoMFA" is a reference to the methodology disclosed in the above referenced patents. Software to perform topomeric fragment alignments and compute their steric fields was disclosed as part of U.S. Pat. No. 6,185,506. Software to perform topomeric fragment alignments of chiral fragments and to generate and search a Virtual Library of molecular components was disclosed as part of U.S. Pat. No. 6,240,374. Not all the software code provided in the cited patents is required to practice the method of the present invention. (As an example, code providing for the calculation of Tanimoto metric values is not required.) Updated versions of all code required (in the computational environment specified herein) to practice the present invention as well as new code to implement the additional features found in the present invention are disclosed in the attached software appendices. Unless otherwise noted, all software references and commands in the following text and software appendices are references to functionalities contained in the SYBYL (including the CoMFA module) and UNITY software programs. The entire disclosures of U.S. Pat. No. 5,025,388, U.S. Pat. No. 5,307,287, U.S. Pat. No. 6,185,506, and U.S. Pat. No. 6,240,374, including the software code filed as part of each application, are incorporated herein as if fully set forth.

A general purpose programmable digital computer with ample amounts of memory and hard disk storage is required for the implementation of this invention. In performing the methods of this invention, representations of thousands of molecules and molecular structures as well as other data may need to be stored simultaneously in the random access memory of the computer or in rapidly available permanent storage. The inventors use a Silicon Graphics, Inc. Challenge-M computer having a single 150 Mhz R4400 processor with 128 Mb memory and 4 Gb hard disk storage space. As the size of the Virtual Library increases, a corresponding increase in hard disk storage and computational power is required. For these tasks, access to several gigabytes of storage and Silicon Graphics, Inc. processors in the R4400 to R10000 range is useful.

B. Definitions

In U.S. Pat. No. 6,185,506 and U.S. Pat. No. 6,240,374 a molecular descriptor (metric) was described which consisted of the steric field values generated at all lattice points in a three-dimensional grid between a probe atom and a molecular fragment having a topomerically (rule-generated) conformation. At the time of writing those patent applications, the term used to describe the metric was "topomeric CoMFA metric." Use of the term "topomeric" was made to reference the conformation of the fragment. Use of the term "CoMFA" was made to reference a field generated at all lattice points in a surrounding three-dimensional grid. At that time, the inventors had no idea that the steric and electrostatic field values about a topomerically aligned fragment could be utilized in a methodology with the previously developed CoMFA technology to yield a valid CoMFA model, and much less, that the term "topomeric CoMFA" would, in fact, be the useful descriptive name for that methodology. In this patent document, the term "topomeric CoMFA metric" is no longer used to refer to the metric consisting of steric fields about a topomerically aligned fragment. When the metric is referenced, it is referred to as the metric consisting of the steric fields about a topomerically aligned fragment. The term "topomeric CoMFA" is now used exclusively to refer to the methodology of the present invention.

TOPOMERIC CoMFA shall mean a comparative molecular field analysis performed using the steric and electrostatic fields of topomerically aligned fragments.

STANDARD CoMFA shall mean a comparative molecular field analysis performed using the steric and electrostatic fields of aligned whole molecules as taught in U.S. Pat. No. 5,025,388 and U.S. Pat. No. 5,307,287

C. Alignment

As pointed out above and in U.S. Pat. No. 5,025,388 and U.S. Pat. No. 5,307,287, and well recognized by those skilled in the art, a major difficulty in performing a CoMFA procedure is the difficulty in aligning the molecules. An absolute three dimensional conformation must be defined for each molecule, and that molecule then aligned with respect to all the other molecules in the activity series. A slight shift to accommodate a difference in one part of a molecule may move other parts out of alignment with the remaining molecules of the series. In some cases, experimentally derived receptor-bound conformations of molecules have been determined and alignment using these data produce excellent CoMFA results. Most often, however, such receptor-bond data are not available and some other alignment method must be used.

The first major advantage of the present invention over the prior art lies in the fact that extensive, complicated, and tedious alignment procedures are unnecessary. Rather a computer implemented alignment method can be employed which can rapidly perform alignments and generate a CoMFA model built upon those alignments.

1. Fragments

A principle discovery disclosed in this patent application is that for certain classes of molecules for which fragment structures can be identified, topomeric alignment of those fragments may be used to generate a useful CoMFA model. This new methodology will be referred to as "topomeric CoMFA." By fragment is meant a chemical structure having an open valence (attachment bond) at one position. Thus, as one type of example, reactants (reagents) before their involvement in a chemical reaction will not have an open valence, but will have that valence position filled with an atom or atoms which are discarded during the reaction and not found in the final product. The fragment is that part of the reactant remaining after the discard of the atom or atoms from the valence position. Fragments by this definition may exist only transiently or not at all in an actual chemical reaction. However, for computational purposes, they can be handled directly. Such fragments have also been referred to as "structural variations" when they were discussed in U.S. Pat. No. 6,185,506 and U.S. Pat. No. 6,240,374 in the context of combinatorial chemistry libraries. For purposes of this patent document the term "fragment" will be employed to refer to all the above cases. It should be understood that fragments need not be derived from reactants. Any part of a chemical structure which can be severed from the remaining structure so as to have one or more open valences (partial bonds) can be considered as a fragment whether or not a reactant exists having the same structure. Fragments are a useful way to deconstruct the three dimensional shape of molecules so that similar parts of molecules can be compared across an activity series.

Figure 3:
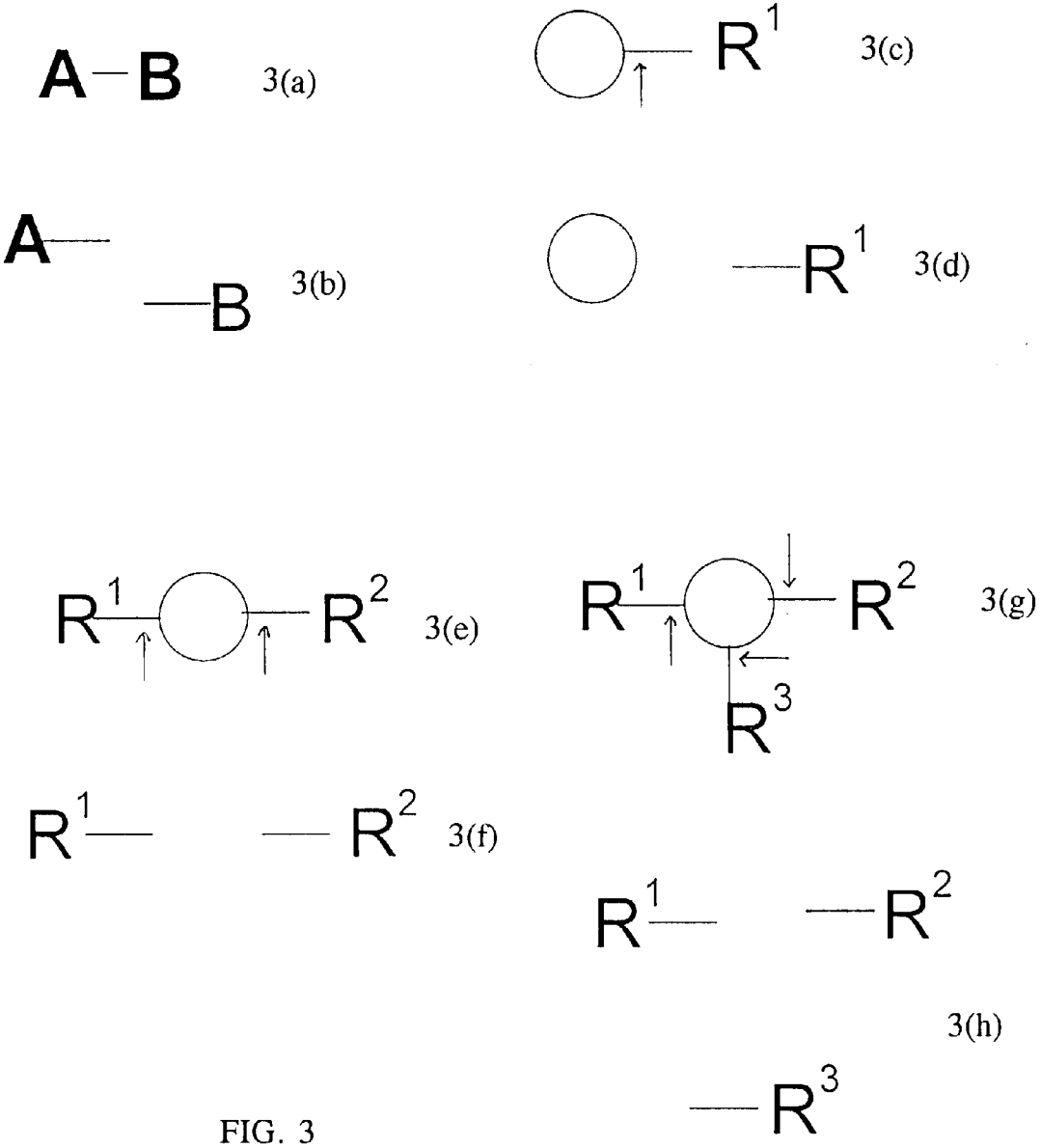
FIG. 3(a), 3(c), 3(e), and 3(g) schematically illustrate some of the possible classes of molecules for which fragments can be identified.
FIG. 3(b), 3(d), 3(f), and 3(h) schematically illustrate the fragments.

Fragments can not be identified in all classes of molecules. However, the power of the present invention can be directly applied to two major classes. The first class comprises those compounds having a variety of side chains attached to a common core. This is a purely congeneric series, for example a combinatorial library sharing a common core. Differences between molecules in this series result from differences in the side chains. This is shown schematically in FIG. 3(c), FIG. 3(e), and FIG. 3(g) where the circle represents a common core not necessarily a cyclic structure. Here the variable side chains can be "clipped off" the common core at points indicted by the arrows in FIG. 3 to become the fragments of FIG. 3(d), FIG. 3(f), and FIG. 3(h) which can be aligned by the topomeric alignment rules.

With a common core, determining the fragments is straight forward by picking out the largest invariant set of atoms. There is a possible complication that the largest invariant set of atoms might be contained within a larger cyclic system for some, but not necessarily for all, molecules of a series. If this should be the case, there are other approaches to take, such as multiple fragmentation (cutting the molecule at two or more bonds), but for combinatorial libraries this complication will not be frequently encountered. Another example of the fragmentation of this class in shown in FIG. 4(a) and FIG. 4(b).

A second class of compounds to which the present invention can be applied consists of roughly homologous series of molecules, with each individual structure consisting of more than one large group connect by one or more acyclic bonds, but with none of those large groups identical throughout the series. This case may be considered as similar to the first class, except that the largest "common core" comprises only one of the acyclic connecting bonds. Thus, two fragments are produced simply by splitting each series member at a chosen acyclic bond. This is schematically illustrated in FIG. 3(a) and FIG. 3(b). If there is more than one acyclic bond to choose from at which to split the molecule, the bond should be chosen to minimize the differences among the resulting fragments across the data set. When selecting a single acyclic bond, the objective is to identify the most similar fragments as similarly as possible. One method of doing this is to pick the bond which is closest to the largest and least variant ring system. This is illustrated in the example shown in FIG. 4(c) and FIG. 4(d).

As with standard CoMFA in which those skilled in the art select members and conformations for members of a series, in topomeric CoMFA the identification/selection of fragments is also determined by the user depending on the particular class of compounds involved.

Two other classes of molecules do not readily lead to identifiable fragments and generally can not be directly handled by the method of this invention. The first of these classes is that of a roughly homologous series containing only one large group which is similar, though not identical, across the series. A good example of such a series is the steroid data set which, after the introduction of the CoMFA methodology, has become a de facto benchmark for subsequent 3D-QSAR methodologies. Such series are poorly suited for fragmentation and topomeric alignment since the few acyclic bonds are not structurally central. These structures can be handled in standard CoMFA by other methods. However, with molecules of particular series, it may be possible to fragment the molecules at two or more different places. As an example, such a procedure could be used to show the shape similarities between the Tamoxifen molecule and typical steroids such as estrogen. Since the topomeric CoMFA method of the present invention is not limited to the number of fragments it can utilize, in appropriate cases more complex molecules may be handled by multiple fragmentations.

A second class of molecules which can not be handled by the method of the present invention is a series having negligible homology. The absence of recognizable commonalities or fragments makes dubious any sort of alignment procedure. However, it may be possible to identify subseries of such molecules having active individual members each having a structural commonality such as seen in the first two classes. The methodology of this invention could then be applied to the subseries.

2. General Topomeric Alignment:

The idea of applying a rule based alignment procedure ("Topomeric Alignment") to align molecular fragments in a uniform manner and a method of implementing such a rule based procedure to generate the topomeric alignment of each fragment and compute its steric field descriptor was first set forth in U.S. Pat. No. 6,240,374. In the preferred embodiment of the topomeric protocol currently implemented by the inventors, the goal is that each conformational adjustment of the fragment implemented by the protocol will direct away from the fragment attachment bond the most important ("highest precedent") as-yet-unadjusted group and will direct the second most important group to the right of the most important group. The aspects of conformation that are adjusted to achieve this goal are torsional (dihedral) angles of acyclic bonds, chiralities of acyclic atoms, and the "puckers" of non-planar rings. The exact protocol rules may be modified for specific circumstances. In fact, once it is appreciated from the teaching of this invention that a particular topomeric protocol is useful (yields a valid CoMFA model), other such protocols may be designed, and their use is considered within the teaching of this disclosure.

Before any alignment protocol can be applied to fragments, it is necessary to standardize the orientations of the fragments in space. The first step in topomer generation is to orient the fragment into a defined, absolute position in Cartesian space, by overlay of the one structural attribute that is by definition found in every fragment, its open valence. This is accomplished by joining the fragment to a standardized template 3D model to fill the open valence of the fragment. The Concord software program is next used to generate a three dimensional model which is then FIT as a rigid body onto a template 3D model by least-squares minimization of the distances between structurally corresponding atoms. By convention, the template model is originally oriented so that one of its atoms is at the Cartesian origin, a second lies along the X axis, and a third lies in the XY plane. It may be necessary to perform small additional rotations to insure that the second and third atoms are located exactly as described above. The effect of this procedure is to ensure that every possible fragment, whatever its chemical structure, will be oriented in the same standard fashion in Cartesian space, exactly superimposing the open valence vector of each fragment.

Each type of conformational adjustment required to complete the topomeric alignment will first be generally described. The precedence rules employed will then be discussed. Finally, a more detailed description of the application of the topomeric alignment protocol be described.

Aspects/classes of Conformational Adjustment:

Torsion Angles:

Rotations about an acyclic bond between two atoms will determine the dihedral angle between two planes defined by: 1) an atom bonded to a first atom forming the acyclic bond; 2) the first atom forming the acyclic bond; 3) the second atom forming the alcyclic bond; and 4) an atom bonded to the second atom forming the acyclic bond. Thus, to unambiguously modify the dihedral angle about the acylic bond, four atoms must be examined. (as an example: in a fragment a-b-c-d containing the acyclic bond b-c, atoms a and d are required to set the dihedral angle.) Precedence rules are necessary to correctly identify which two additional atoms on each side of the acyclic bond are to be used.

Chiral and Equivalent Atoms:

Chiral atoms have four different moieties attached to them. Clearly, selection rules for orienting four different possible moieties are necessary. However, the problem remains even if less than four different moieties are attached, and a specialized topomeric alignment rule must be adopted for any tetrahedral atom that bears two non-identical attached moieties to resolve the ambiguity. Such tetrahedral atoms include atoms that do not possess chiral centers such as the secondary carbon in —CH(CH3)CH3 and any trivalent pyramidal nitrogen atom. For purposes of this application, references to "Chiral Atoms or Chiralities" should be understood to include the above atom types. The specialized topomeric alignment rule for chiral atoms is not applied for chiral atoms found in ring structures.

Puckered Rings:

Two energetically equivalent orientations of a puckered non-planar ring exist which are related by a reflection. Consider as an example the conformation of the idealized boat form of cyclohexane, which can be reflected through the plane of its 1,2,4,5 atoms.

Each of these orientations places atoms in different spatial locations and the topomeric protocol is standardized to utilize only one of the two energetically equivalent reflections.

Precedence Rules:

The following precedence rules provide the ordering among attachment atoms necessary for the assignments of individual torsions and chiralities. From each candidate atom, begin growing a "path", atom layer by atom layer, including all branches but ending whenever another path is encountered (occurrence of ring closure). The precedence among attachment atoms will be determined by the precedences of their paths, as will now be detailed. The highest precedent paths will always be the shortest paths leading to an open valence atom, if such a path exists. If there is more than one such atom, as in polyvalent fragments, then the highest precedent path will be that leading to the root atom. If there are more than two such atoms (tri- and higher valent fragments), precedence among those remaining is determined by the general rules, now to be described. The highest precedent path is that containing the most atoms. When two paths contain the same number of atoms, the path having the highest molecular weight takes higher precedence. When two paths have the same molecular weight but a different topology, for example within the 2,5-xylyl (2,5-dimethylphenyl) fragment shown below, the higher precedence belongs to the path that puts most mass nearest the fragment root (determined by the larger of the sum of atomic weights divided by the number of connecting bonds for each path). In the example shown, the path including the 2-methyl group is chosen.

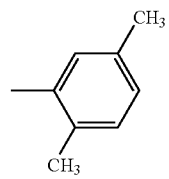

When two paths are topologically indistinguishable, it is still necessary in order to define the dihedral angle to define a precedence, inasmuch as the alternative possibilities will often yield very different topomeric conformations. Consider the following structure:

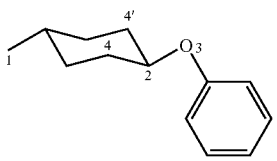

Depending on whether the 4 or 4' position is used to set the dihedral angle, different topological orientations will be generated. The solution, which has been adopted, is to examine the angles between the plane defined by atoms 1-2-3 and the planes defined by 2-3-4 and 2-3-4' as illustrated in the figure below. The "4" atom which is selected to set the dihedral angle is the "4" atom in either the plane 2-3-4 or 2-3-4' which makes an angle greater than 180 degrees to the 1-2-3 plane.

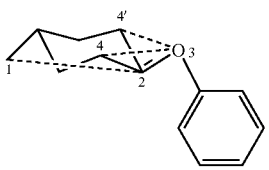

A further complication arises from the goal of always placing the highest precedent attachment available "to the right" of the growing topomer conformation. Achievement of this goal is not straightforward. For example, if the side chain methyl groups in —CH(CH3)CH(CH3)Ph are positioned by ensuring only that the torsional angles of both are 60 degrees with respect to the all-trans (topomeric) main chain bonds toward the root, it will be found that the methyl groups are located on the opposite rather than the same sides of that main chain. The solution to this problem is discussed below.

Details of Conformational Adjustments:
Conformational Adjustment—Torsions:

As mentioned earlier, within a molecular structure, a dihedral angle may be defined only by the specification of four consecutively connected atoms. In the generation of a topomer, the "1" and "4" (first and last of the four) atoms are always identified by application of the precedence rules as detailed above. (The "2" and "3" atoms are the endpoints of the bond whose torsion is being modified.) Also, the "2"=>"3" direction or order is always such that the "2" atom is the one closer to the root or fragment attachment point. The value that a torsion angle takes within a topomer depends on whether the "1"=>"2" and "3"=>"4" bonds are contained within rings. If neither of the two bonds is in a ring, the torsion angle is modified to 180 degrees, if either is in a ring the torsion angle becomes 90 degrees, and if both are in a ring the specified torsion angle becomes 60 degrees.

Figure 5:
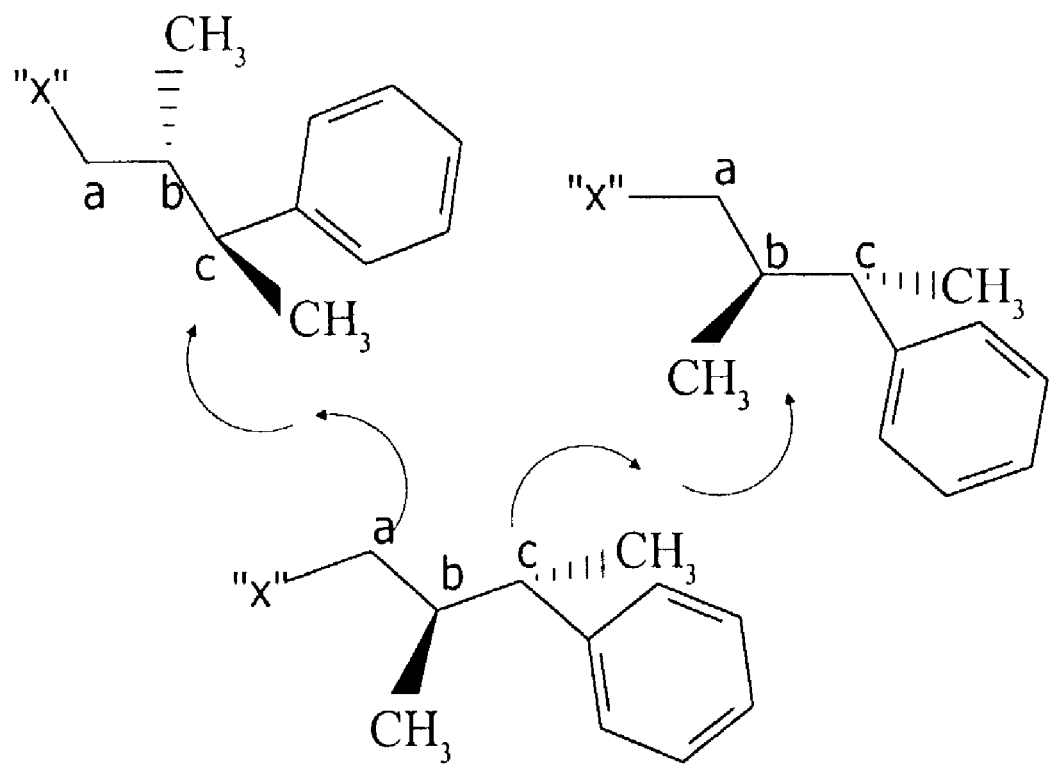
FIG. 5 illustrates the rotations in three dimensions to achieve the correct topomeric alignment.

Conformational Adjustment—Chirality:

The general procedure for assuring that the higher precedent of two non-equivalent attachments to a "chiral" atom be positioned to the right of a specified bond will now be described. For this purpose, the "right-side" positioning objective can be restated as "if the specified bond is placed on the X-axis so that the atom closet to the root has the lowest X value in the X-Y plane, then the "right-side" position corresponds to a positive Z-coordinate for the higher precedent attachment atom." Since there may be a further complication as discussed below, a temporary copy of the fragment is generated and used as a test. See FIG. 5 for examples of this repositioning for each of the two CH3 groups in the —CH(CH3)CH(CH3)Ph fragment earlier mentioned. (The initial fragment alignment is shown at the bottom.) However, there is a further complication in that the repositioning procedure in the molecular modeling system in which the topomeric alignment is being implemented may achieve the repositioning result by rotating the entire structure by 180 degrees around the specified bond (as shown for the top left hand repositioned structure in FIG. 5 [rotation around bond b-c]). Whenever this happens the "right-side" positioning for the side chain requires a negative Z-coordinate for the higher precedent attached atom. The SYBYL repositioning procedure performs the additional rotation described above whenever the Y coordinate of the further atom "b" in the specified bond is less than the Y coordinate of the closer atom "a" (again as shown for the left hand repositioned structure in FIG. 5). Other repositioning procedures may require a different convention. In either situation, if the Z coordinate of the higher precedent atom has a sign opposite from that which is required for "right-side" positioning, the topomeric protocol requires that the non-equivalent attachments are reflected through the plane defined by the specified bond (a-b) end-points and the attachment atom along the path leading to the fragment root position "x", drawn so that the first $CH^3$ does not need reflection but the second $CH^3$ will need reflection.

Conformational Adjustment—Ring Pucker:

The methodology of the preferred embodiment used for standardizing ring "pucker" will now be described. As noted above, two energetically equivalent orientations of a puckered ring exist which are related by a reflection. Each of these orientations places atoms in different spatial locations and the topomeric protocol is designed to utilize only one of the two orientations. Therefore, after any (acyclic) dihedral angle has been processed, its 3-4 bond is checked for inclusion in a ring. If a new ring system is thereby found, all of the atoms in that ring system are identified, the least-squares plane through that ring system is constructed, and the sum of the heights of all ring atoms above this plane is computed. If this sum is greater than 0.5 A°, the ring is non-planar and may need standardization. Whether or not the ring needs conformational adjustment is determined by examining the dihedral angle for the root-3-4-(ring-system-centroid) torsion. If the dihedral angles is less than 180 degrees, no conformational adjustment is made. If this dihedral angle is greater than 180 degrees, the coordinates of all atoms in the ring system, including all its more distant attachments, are reflected through the plane formed by the 2-3-4 atoms of the original dihedral angle.

Example of Application of Conformational Adjustment Protocol:

The overall methodology of standardizing torsions, "chiralities", and ring puckering, using the precedence rules, will now be described and exemplified. First, a list of all acyclic tetrahedral atoms attached to at least two other atoms is assembled. To this list are added any cyclic atoms that are at the ends of acyclic single bonds. The list of atoms is sorted in increasing order of the number of bonds separating each atom from the fragment attachment bond. Topomer generation is then accomplished by the traversal of this sorted atom list (essentially walking away from the root), each atom in turn being fully processed as follows. The highest precedence attachment to the current atom (excluding the path back to the root) is identified, according to the rules previously set forth. If there are two non-identical attachments remaining, or only one attachment (as when the current tetrahedral atom is nitrogen), then the "chirality" must be standardized as previously set forth. Then each of the bonds connecting the current atom to an attachment is considered as a candidate for torsional adjustment (again except for the path leading back to the root, as the torsion of that bond will if necessary have been adjusted in connection with a previous "current atom"). Torsional adjustment is then performed as detailed, using the precedence rules to identify the 1 and 4 attachments. Finally, if the 3-4 bond of a torsion is included in a ring system, the ring system is subjected to the puckering standardization previously described.

Figure 6:
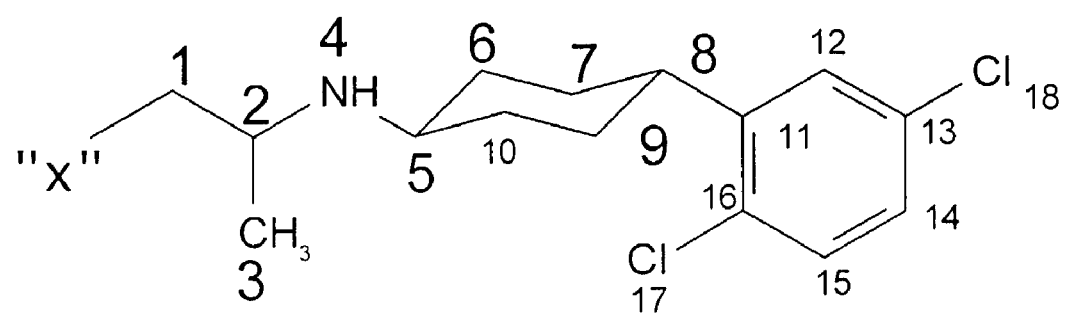
FIG. 6 is a molecule examplifying the requirement for the application of all the topomeric alignment rules.

To further illustrate the process of topomer generation, the topomeric alignment of the fragment example in FIG. 6 will be described. The root or attachment point position is on the left, the position being indicated by "x". Most of the hydrogens are not shown for simplicity, as they seldom affect the resulting topomer conformation. It may be seen that tetrahedral atoms attached to at least two other atoms by acyclic bonds are atoms 1, 2, 3, and 4. There is also an acyclic bond between atoms 8-11, so the final list of atoms to be traversed during topomer generation is 1, 2, 3, 4, and 8. Proceeding in order down this list:

Atom 1. Its highest precedent attachment (excluding the root) is the remainder of the fragment; its other two attachments, the hydrogens not shown, are identical, and so no "chirality" operation is needed. The 1-2 bond needs its torsional angle set, and so the precedence of the attachments to the 1-2 bonds must be established. The first precedence rule "take the path to the root" establishes the position designated by "x"_as the "1" atom (the first of the four atoms/positions required to set a dihedral angle), while the next precedence rule "take the attachment with the most atoms" clearly favors atom 4 over atom 3 as the "4" atom. Therefore the dihedral angle of the x-1-2-4 bond is changed to 180 degrees, to appear much as shown. The 2-4 bond is not in a ring so no pucker adjustment need be considered.

Atom 2. Its highest precedent attachment (excluding the root) is again the remainder of the fragment. However atom 2 is chiral—the 3 atom (the methyl) is evidently not equivalent to the unshown hydrogen. Therefore the chirality standardization procedure described above is applied to atom 2. There are two bonds away from atom 2 whose torsions need attention, 2-3 and 2-4. In both cases atom 1 as the shortest path to the root becomes the "1" atom. All of the attachments to atom 3 (hydrogens) are equivalent in precedence, so the selection of the "4" atom is completely random, the topomer geometry of course being identical regardless of which hydrogen becomes the "4" atom in the setting of 1-2-3-H to 180 degrees. Having taken account of the chirality, the dihedral angle about 2-4 can now be addressed. There are two attachments to atom 4, the hydrogen and the rest of the fragment, the latter having higher precedence because it has more atoms so that it is the 1-2-4-5 dihedral which is set to 180 degrees, again.

Atom 4. Its highest precedent attachment (excluding the root) is again the remainder of the fragment. There is only one other attachment to 4, the hydrogen as shown. Since there is only one attachment, the "chirality" of 4 must be adjusted as described above (ensuring that the hydrogen is located to the right of the main chain), even though the nitrogen is not chiral by the usual definition. There is one torsional angle to be established, the "1" atom again being the path back to the route. However the selection of the "4" atom is complicated.

It will be evident that the paths away from atom 5, beginning with atoms 6 and 10, are topologically identical. (As noted earlier, path generation stops when another path is encountered, any overlapping atom(s) being discarded. In this case atom 8 ends both paths.) However the paths are not geometrically equivalent, in that a rotation about 2-4-5-6 will yield a geometry different from the equivalent rotation about 2-4-5-10. So the precedence rules outlined earlier will yield an unambiguous geometry, selecting as the higher precedent attachment the one whose x-4-5-? dihedral value is greater than 180 degrees. In this instance, the higher precedent atom will be 6 and the 2-4-5-6 dihedral value will be the one set. However, because the 5-6 bond is in a ring, the 2-4-5-6 bond is set to 90 degrees, not 180 degrees.

The other consequence of the 5-6 bond being in a ring is that the pucker state of that ring must be standardized. The ring system is found to include atoms 5 through 10 (the 8-11 bond is not in a ring and so the phenyl group is not part of the same ring system). The ring pucker adjustment method will indicate that atoms 5 through 10 do not lie in a plane, and so the dihedral angle x-5-10-(ring centroid) is evaluated. If this value is greater than 180 degrees, the coordinates of all the remaining atoms 5 through 18 are reflected through the 4-5-10 plane.

Atom 8. The chiral operation is not applied because atom 8 is contained in a ring. To establish the dihedral angle about bond 8-11, the precedence rules must choose between atoms 7 and 9 as the "1" atom and between atoms 12 and 16 as the "4" atom. Because the paths leading from the 7 and 9 atoms are topologically identical, the dihedral angles x-8-11-7 and x-8-11-9 will be calculated, and the higher precedence will be associated with the path whose dihedral is greater than 180 degrees and thereby identify the "1" atom. The paths leading away from atoms 12 and 16 have the same numbers of atoms and the same molecular weights. However the sums of the atomic weights divided by the bond separations will not be equal (as a consequence of their topological difference), and so atom 16 will have higher precedence and become the "4" atom of the dihedral angle. The complete dihedral angle to be set is 7-8-11-16, and the value that its dihedral will take is 60 degrees, since both the 7-8 and 11-16 bonds are contained within rings.

Because the 11-16 bond is contained within a ring, the ring system including atoms 11 through 16 will be evaluated, found to be planar, and thereby require no pucker adjustment for standardization.

Using the selection rules set out above, the critical point is that the topomerically defined fragment conformers, which provide uniform conformations over a series of fragments, may be used to compute three dimensional descriptors which, in turn, can be used to compare the shapes of the fragments. While other approaches to conformer selection such as averaging many representative conformers or classifying a representative set by their possible interactions with a theoretically averaged receptor (such as in the polyomino docking) are possible, it has been found that the steric fields about topomerically aligned conformers yield a validated descriptor. It should be further understood, that there may be other rule based alignment procedures which produce equally satisfactory results to the topomeric alignment.

D. Calculation Of CoMFA Fields

The basic CoMFA methodology provides for the calculation and use of both steric and electrostatic fields and this procedure is followed for topomeric CoMFA.

The fields of the topomerically aligned fragments are generated almost exactly as in a standard CoMFA analysis using an $sp^3$ carbon atom as the probe for the steric fields and a negative oxygen atom as the probe for the electrostatic fields. As in standard CoMFA, both the lattice spacing and the size of the lattice space for which data points are calculated will depend on the size of the fragment and the resolution desired. The steric fields are set at a cutoff value (maximum value) as in standard CoMFA for lattice points whose total steric interaction with any fragment atoms is greater than the cutoff value.

One difference from the standard CoMFA field generation procedure is that atoms which are separated from any template-matching atom by one or more rotatable bonds are set to make reduced contributions to the overall steric and electrostatic fields. An attenuation factor (1—"small number"), preferably about 0.85, is applied to the steric and electrostatic field contributions which result from these atoms. For atoms at the end of a long fragment, the attenuation factor produces very small field contributions (ie: $[0.85]^N$) where N is the number of rotatable bonds between the specified atom and the alignment template atom. This attenuation factor is applied in recognition of the fact that the rotation of the atoms provides for a flexibility of the fragment which permits the parts of the fragment furthest away from the point of attachment to assume whatever orientation may be imposed by the unknown receptor. If such atoms were weighted equally, the contributions to the fields of the significant steric differences due to the more anchored atoms (whose disposition in the volume defined by the receptor site is most critical) would be overshadowed by the effects of these flexible atoms.

For computational convenience, one further variation of the calculated steric and electrostatic fields is employed to reduce the size of the fields which must be stored. The calculated steric interaction values, which are all positive, associated with each lattice point are binned into 1 of 15 levels. A 16th level is used to indicated the absence of any steric interaction value. The electrostatic field values are also binned but since they can take on both negative and positive values, the bin values run in 15 equal increments from bin 1 for electrostatic field values less than −13, bin 2 for values between −13 and −11, etc. through 0 to bin 16 to represent positive electrostatic field values greater than +13.

It should be noted that the standard CoMFA fields, non-attenuated and non-binned, could just as well be used in the topomeric CoMFA methodology of the present invention. However, as mentioned above, for computational convenience binned CoMFA fields have been utilized.

E. Inclusion of Features Data

A useful characterization of molecular fragments may also be implemented for use with the present invention which extends ideas from pharmacophore modeling for use in searching Virtual Libraries of compounds. It is well recognized that certain characteristic interactions of molecules in addition to shape play an important role in determining whether that molecule will bind to a larger biomolecule. Complementarity of shape permits the molecules to approach each other closely enough for these interactions to take place. In pharmacophore modeling the presence and location of feature classes containing molecular characteristics thought important to the binding of the molecule is tracked as well as the distances and directions between the features. An absence of any given feature in a molecule or a different location is considered to significantly reduce the likelihood of that molecule's binding and, thus, typical pharmacophore modeling is an all or nothing proposition. Clearly, in the present methodology due to the topomeric alignment of fragments all distance and direction attributes of features present in the fragments are lost.

However, an additional inventive aspect of the present invention is that an alternative approach to incorporating the characteristic interactions in conjunction with the shape similarity matching described below has proven to generate an exceedingly powerful and accurate discovery methodology. The classic five feature classes are employed: positive charge, negative charge, hydrogen-bond-donating, hydrogen-bond-accepting, and aromatic. When present in either a fragment derived from a molecule in the activity series or a fragment characterized in the Virtual Library, the features are assigned x,y,z point locations in the topomer alignment either centered on the relevant atom, or, in the case of aromatic rings, the centroid of the ring is specified. Generating the topomer conformation of a molecular fragment not only fixes the steric shape of that fragment, but also fixes the Cartesian coordinates of each pharmacophoric feature contained within the fragment. The methods for searching feature data will be described below. The software code to associate feature data with fragments in a Virtual Library is also included in the Appendices.

F. Generation of Topomeric CoMFA Data Tables

The arrangement of the data tables for topomeric CoMFA differs only slightly from standard CoMFA due to the use of fragments rather than whole molecules. Four cases will be illustrated by way of example. For topomeric CoMFA each fragment is identified by its own set of steric and electrostatic CoMFA columns, but all columns across all fragments are used to generate the CoMFA QSAR model. Examples of the data table construction are given below. First, consider the class of molecules of the roughly homologous series described above and shown schematically in FIG. 3(a) and FIG. 4(b). Two fragments will be generated for each molecule of the series. The field descriptors for each fragment are placed in appropriate columns of the data table as follows:

|  | Measured | Fragment No. 1 | | Fragment No. 2 | |
| --- | --- | --- | --- | --- | --- |
| Mol. ID | Parameter | Steric | Electrostatic | Steric | Electrostatic |
| Mol. 1 | $V_1$ | | | | |
| Mol. 2 | $V_2$ | | | | |
| Mol. 3 | $V_3$ | | | | |
| ... | | | | | |

In these tables the dotted vertical lines under each field heading schematically represent the several thousand columns corresponding to all the lattice points which are employed—a separate column being used corresponding to each lattice point. The dashed line across the bottom of the table schematically represents the inclusion of as many additional rows as there are compounds in an activity series. Only 3 molecules are represented in these schematic tables.

Second, consider the case of a molecule having a common core and only one variable side chain as shown in FIG. 3(c). Clipping off the side chain produces one fragment whose field values are placed in the data table as follows:

|         |          | Fragment |               |
|---------|----------|----------|---------------|
| Mol. ID | Measured Parameter | Steric | Electrostatic |
| Mol. 1  | $V_1$    |          |               |
| Mol. 2  | $V_2$    |          |               |
| Mol. 3  | $V_3$    |          |               |
| ...     |          |          |               |

No field values are entered for the common core since the invariant common core can not contribute any difference to the activity of the molecules across the series.

Figure 4:
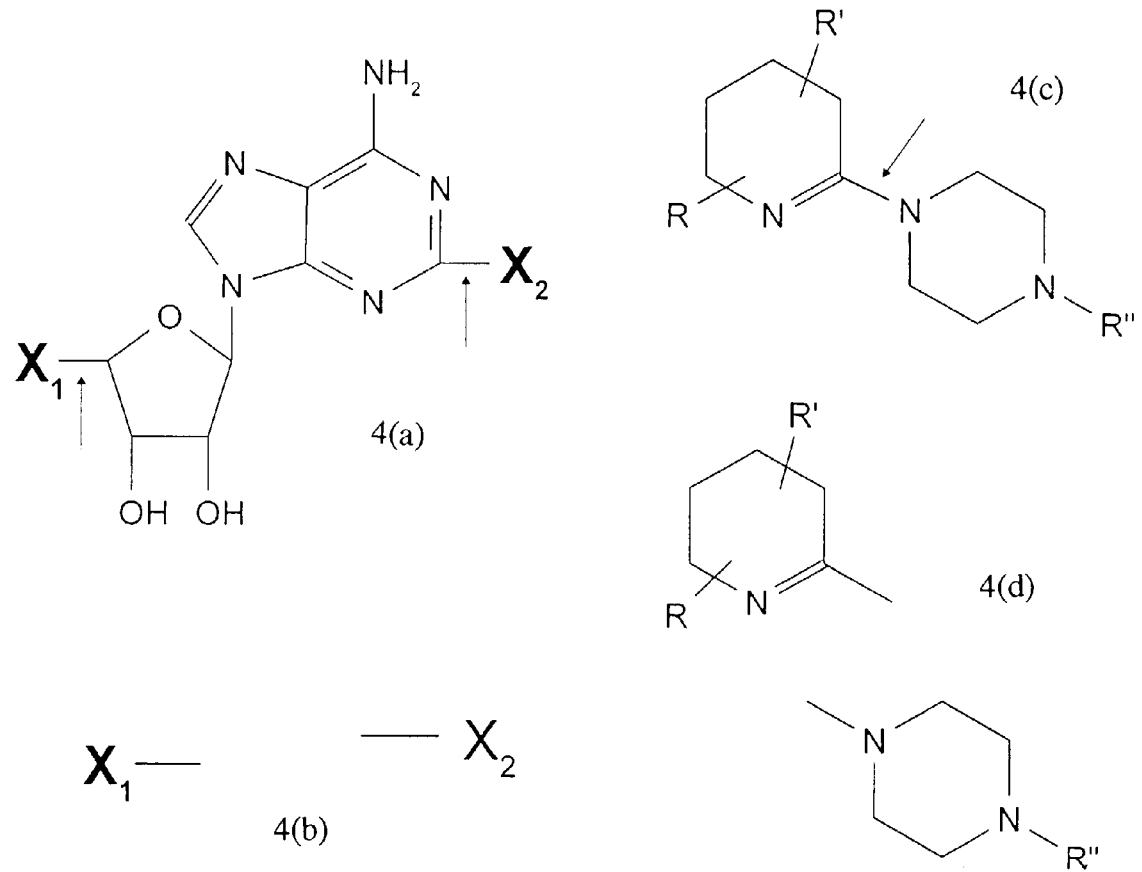
FIG. 4(a) and FIG. 4(b) illustrate fragmentation of two side groups from a central chemical core structure.
FIG. 4(c) and FIG. 4(d) illustrate fragmentation at an acyclic bond between two ring systems.

Third, consider the case of a molecule having a common core and two variable side chains as shown in FIG. 3(e) and FIG. 4(a). Generating the fragments by clipping off the side chains, FIGS. 3(f) and FIG. 4(b), produces a data table similar to the first example above with two fragments whose field values are placed in the data table as follows:

|         | Measured  | Fragment No. 1 | | Fragment No. 2 | |
|---------|-----------|--------|---------------|--------|---------------|
| Mol. ID | Parameter | Steric | Electrostatic | Steric | Electrostatic |
| Mol. 1  | $V_1$     |        |               |        |               |
| Mol. 2  | $V_2$     |        |               |        |               |
| Mol. 3  | $V_3$     |        |               |        |               |
| ...     |           |        |               |        |               |

Again, no field values are entered for the invariant common core.

Fourth, consider the case of a molecule having a common core and three variable side chains as shown schematically in FIG. 3(g). Clipping off the side chains produces three fragments, FIG. 3(h), whose field values are placed in the data table as follows:

|         |           | Fragment No. 1 | | Fragment No. 2 | | Fragment No. 3 | |
|---------|-----------|--------|----------|--------|----------|--------|----------|
| Mol. ID | Measured Parameter | Steric | Electro-static | Steric | Electro-static | Steric | Electro-static |
| Mol. 1  | $V_1$     |        |          |        |          |        |          |
| Mol. 2  | $V_2$     |        |          |        |          |        |          |
| Mol. 3  | $V_3$     |        |          |        |          |        |          |
| ...     |           |        |          |        |          |        |          |

Again, no field values are entered for the invariant common core. Thus, it can be seen that field values are entered into a CoMFA data table only for those fragments which have been derived from each molecule. Clearly, no limit is placed on the topomeric CoMFA methodology by the number of fragments to be included and the data table can be extended to provide for any number of fragments. As in standard CoMFA, the data table may also contain any additional information in additional columns which is considered relevant to the measured activity.

G. Topomeric CoMFA Models

PLS with cyclic cross-validation applied to the data tables in the conventional manner described in U.S. Pat. No. 5,025,388 and U.S. Pat. No. 5,307,287 generates a topomeric CoMFA model. As with standard CoMFA, PLS produces in topomeric CoMFA a set of coefficients (one for each column in the data table) which reflect that position's influence on the observed activities. Quite surprisingly in view of the prior art emphasis on alignment requirements for practicing CoMFA, robust CoMFA models are produced by the topomeric CoMFA methodology. Topomeric CoMFA was applied to 15 recent literature studies (for which fragments could be identified among the molecules) which reported results using standard CoMFA with a variety of alignment methods. The literature studies used are set forth in Table 1 in FIG. 7. In 15 out of the 15 literature studies, the topomeric CoMFA model was substantially as good as the model derived from the standard CoMFA methodology. Specifically, the coefficient values determined from application of the topomeric CoMFA method of the present invention are on average substantially as good at predicting the likely activity of molecules in an activity series as were the coefficients derived by the authors of the literature references using standard CoMFA although topomeric CoMFA was better for some series than for others. For eleven of the fifteen datasets (from eight of the eleven publications), the literature CoMFA model had been validated by predicting the potencies of compounds omitted from its development, for a total of 138 compounds. Because of the exemplary practice, comparisons could be made with predictions based on the topomeric CoMFA models. Since one purpose of a CoMFA model is to make accurate predictions about structures not included at all in model derivation, it is particularly important that the average of the prediction errors was slightly less for the topomeric CoMFA models than the average prediction errors for the CoMFA models reported in the literature. The average performance of the automatic topomeric CoMFA models are almost identical to the average literature models as can be seen in Table 2 of FIG. 8. The 15 test sets of literature data also were evaluated both by using the full steric and electrostatic range of interaction energies generated and by using binned energy levels. The resulting topomeric CoMFA models were not significantly different.

The topomeric CoMFA results are surprising since traditional CoMFA has been found to be so sensitive to misalignments. Nowhere does the prior art suggest that such an arbitrary rule based topomeric alignment protocol could possibly yield a meaningful alignment. Indeed, the prior art inherently teaches away from the idea of a single rule-based alignment because the topomerically derived conformers often may be energetically inaccessible and incapable of binding to any receptor. In the topomeric CoMFA method of the present invention, the alignment of fragments is arbitrarily rule based—in one sense the very essence of misalignment. However, as seen when used with molecular structural metrics, the topomeric alignment, while not necessarily reflecting a real world conformation, never-the-less provides a significantly good alignment for comparison purposes. Fundamentally, the topomeric alignment provides that similar topologies should take on similar shapes—topomer alignments do align "like with like." It is also highly probable that all prior art alignment methods used in standard CoMFA (such as docking) displace significant portions of each structure in an attempt to align other portions considered more important. Such displacement introduces arbitrary field differences between the molecules not related to activity (since an invariant core can not cause changes in activity); essentially introducing a certain amount of noise into a standard CoMFA model.

H. Topomeric CoMFA Prediction and Searching

Just as with the standard CoMFA methodology, the coefficients found by PLS in topomeric CoMFA can be used to predict the likely activity of molecules not included in deriving the CoMFA model. This leads to another major advance of topomeric CoMFA over the prior art. One weakness of standard CoMFA has always been that, while identifying which spatial volumes around a molecule are associated with increased or decreased activity, no suggestion is made by the method as to what specific molecular changes (atoms or groups added or subtracted) could be made to take advantage of the CoMFA results. Once a chemist had reviewed the CoMFA results, a varied molecular structure could be intelligently proposed, field values calculated for that structure, and the likely activity predicted by use of the column coefficients.

Topomeric CoMFA, on the other hand, provides an immediate gateway to identification of alternative active structures. A Virtual Library of precomputed characteristics of fragments can be constructed along the lines of that described in U.S. Pat. No. 6,240,374. However, unlike the previously described Virtual Library, no information about: 1) the Tanimoto descriptor; 2) cores; or 3) reactions need be included although the presence of such additional data may enhances the Virtual Library's usefulness with topomeric CoMFA as will be described below. A Virtual Library for use with topomeric CoMFA contains, as a minimum, associated with each fragment both the steric and electrostatic field descriptors derived from the topomeric alignment of the fragment. Standard non-binned fields may be used or binned fields may be used as were described earlier. In addition the library may contain any additional data associated with each fragment which it may be useful to search, for example, the features definition described earlier or data relating to absorption/distribution/metabolic/excretion/toxicity (ADMET) properties desirable for oral activity as well as price and availability.

As a practical matter for computational convenience, the inventors have chosen to use binned fields. Binned electrostatic interaction characterizing data is associated with each fragment in the Virtual Library for use with topomeric CoMFA. In this way, a searchable Virtual Library did not have to be reconstructed and the previously constructed Virtual Library could, with expansion, be utilized.

The format for each fragment in the Virtual Library will appear as:

```
A1C[2]:CH:CH:C(:CH:CH:@2)OCH(CH3)CH3 < FCD="100148";PS_SCORE=" ";
YIELD="100";FCD_LIST="100148";PS_SCORE_LIST=" ";RGTID_LIST="1";
PREF_LIST="0";S2RID_LIST="53";FRAG_IDX="4";MOLW="135.19";LOGP="3.40";
RDB="5";AS="0";DS="1";PROCHIRAL="0";CHIRAL="0";ALLCHIRAL="0";
EXTENT="0";AR="1";NITRO="0";HALOGEN="0";FEATURES=
"1,2.908,-.002,0,1;4,5.678,-.003,0,.85">
1111111111111111111111111111111111111111111111111111111111111111
1111111111111111111111111111111111111111111111111111111111111111
1111111111111111111111111111111111111111111111111111111111111111
11111111111111111111111111111111112cc11111111111111111111111111111
111111111111111111111111111111111111111111111111511111116ff311113ffff1111
bff71111111f111111111111111111111111111111111111111111111111111111
2f21111bf7fff1111ffff51112fff92111119f41111111111111111111111111111111
1111111111111111111111115111112fff3111113ffff11111ff71111118ff1111111111
11111111111111111111111111111111111111111111211111111ff21111111ffc1111
11152111111141111111111111111111111111111111111111111111111111111
111111111121111111112111111111111111111111111111111111111111111
1111111111111111111111111111111111111111111111111111111111111111
1111111111111111111111111111111111111111111111111111111111111111
11111111111111111111111111111111111111111!
1111111
11
8888888888888888888888888888888888888888888888888888888888888888
8888888888888888888888888888888888888888888888888888888888888888
8888888888888888888888888888888888888888888888888888888888888888
888888888888888788888888777888888888999888888999888888999888888888888
888888888888888888888888888888888888788888887778899887745800888874000788
88b008778889ac98888888998888888888888888888888888888888887888888887
66890988761170008876000006888900075788896b0987788888888888888888888888
8888888888888888888888888888777889998877500008888730000788880007678888167
7888888888888888888888888888888888888888888888888888888888888888887800888
88877008888887547788888767788888887788888888888888888888888888888888
888888888888888888888888888888888888888877777888888877888888888888888888
8888888888888888888888888888888888888888888888888888888888888888
8888888888888888888888888888888888888888888888888888888888888888
88888888888888888888888888888888888888888888888888888888888888!
8888888
88
```

The data entries containing all the 8s represent the electrostatic field. As an example of the incorporation of data on features, the last field within the first line contains FEATURES. There can be seen two sets of five numbers separated by a semicolon, describing the HB accepting ether oxygen and the aromatic ring. The first of the five numbers is the feature type; the 2nd through 4th the X,Y,Z coordinates, and the −5th the attenuation factor.)

Once an initial topomeric CoMFA model has been generated (coefficients obtained), the Virtual Library can be searched for fragments similar in shape to the fragments derived from molecules of the activity series used to generate the topomeric CoMFA model. The search methodologies utilizing just the steric field for identifying fragments similar in shape are the same as were described in U.S. Pat. No. 6,240,374. Since the fragments derived from the molecules of the activity series have, by definition, different shapes, the question arises as to which fragments of which molecules should be used as the criterion for the search of the Virtual Library. The inventors have found that the average of the steric field values at each lattice location over all the fragments which were used in generating the topomeric CoMFA model provides excellent search results. Alternatively, a prototypical molecule within the topomeric CoMFA model set could be used. Either way, similarly shaped fragments can be quickly identified from the Virtual Library.

Searching using the metric descriptor consisting of the steric fields about topomerically aligned fragments is accomplished by computing the difference between the average of the steric field values at each lattice point of the model fragments and the field values at corresponding lattice points of each fragment in the Virtual Library. Two values may be calculated. The first value is the simple sum of the differences across all lattice points. The second value is the root mean sum of squares of the differences across all lattice points. In the current implementation of topomeric CoMFA, the inventors follow the previous practice of using the root mean sum of squares. This value provides for immediate comparison to the neighborhood distance for the steric metric. Clearly, the smaller the differences, the more similar the fragments are in shape. Since the metric consisting of the steric fields about topomerically aligned fragments was validated by the Patterson Plot methodology, a neighborhood radius (distance) was determined for the descriptor of 80-100 kcal/mol. This neighborhood distance corresponds to approximately a log 2 difference in biological activity. A larger or smaller distance may be chosen for the search depending on whether greater or lesser similarity is desired in the search results.

For each similarly shaped fragment identified, the previously derived QSAR topomeric CoMFA model column coefficients can be used with the identified fragment's steric and electrostatic field values to generate the partial likely activity of a molecule formed by incorporating that identified fragment. In the preferred embodiment, the identified fragments are initially ranked according to the likely activity predicted from the topomeric CoMFA model. The ranking for each fragment is determined based upon only the field values for that fragment. For instance, in the case of two fragments, $R^1$ and $R^2$, generated from each molecule in the activity series, only the steric and electrostatic column coefficients associated with $R^1$ would be used to generate a partial predicted activity associated with fragments identified in the Virtual Library as similar in shape to $R^1$. Similarly, only the steric and electrostatic column coefficients associated with $R^2$ would be used to generate a partial predicted activity associated with fragments identified in the Virtual Library as similar in shape to $R^2$. As with the choice of a cut-off value for the neighborhood distance used to identify similarly shaped molecules, the user can set a cut-off value of predicted activity in the ranking of the fragments identified from searching the Virtual Library.

To compute a predicted activity of a new molecule having both an $R^1$ and $R^2$ fragments, it is only necessary to combinatorially add the partial predicted activities calculated for each of the highest ranking fragments identified from the Virtual Library. For example, if the activities of three fragments, identified in the Virtual Library as being close in neighborhood distance to the fragments used to generate the topomeric CoMFA model, are ranked in the order A, B, C for $R^1$ and a, b, c for $R^2$, an activity prediction for the 9 possible molecules containing both fragments would be calculated by using the following combinations of partial activities: A+a, A+b, A+c, B+a, B+b, B+c, C+a, C+b, and C+c. Note that the order is important since it refers to position in the molecule; that is, the column coefficients which are used to multiply the fragment field values. It should be appreciated that searches are conducted using the steric field values, but activity predictions are made using both the steric and electrostatic field values.

If the fragments from the molecules of the activity series contain features, a search strategy employing the features data can be summarized as finding all the Virtual Library fragments which have features, similarly located in topomer space and similar in any other detailed feature property, that match each of the features in the topomerized fragments derived from the molecules in the activity series. In keeping with the distance definitions used for steric shape similarity, differences in features are defined with the same dimensionality as shape so that both shape and features can be used to characterize a fragment for searching. Feature by feature differences are also combined in a root sum square rather than a straight sum fashion. Thus, a second feature mismatch would not be as costly as the first one. In the preferred embodiment, to determine the feature "distance", each of the pharmacophoric features in the query structure is considered in turn, by identifying the closest feature of the same pharmacophoric class in the Virtual Library fragment. If there is no such feature or if the nearest such feature is more than 1.5 Å distant, the dissimilarity sum of squares is increased by a maximum of 100×100 units. (Units are chosen to be commensurate with the steric shape units of kcal/mole-Angstrom.) If there is a matching feature within 0.5 Å, the dissimilarity is set to zero. For a feature separation between 0.5 Å and 1.5 Å the dissimilarity penalty increment is obtained by linear interpolation between 0 and 100×100 unit values. Further, it is possible to scale/weight the feature contribution to increase or decrease its relative contribution with respect to the steric contribution to the observed similarity (distance). Note that the use of the term "distance" with the feature searching methodology of the present invention is not meant to refer to an actual physical "distance" as considered in traditional pharmacophore techniques Feature matching for the appropriate molecules has been found to greatly increase the effectiveness of Virtual Library searching since it compliments the shape specific searching. In addition, the results of shape and feature similarity searching yields actual molecular structures which chemists recognize as being members of the same class of compounds.

The software code provided automatically computes the average of the steric field values at each lattice point, performs a search through the Virtual Library, computes the resulting activity predictions, reports the results in rank order of the most active fragments found in the search, and reports the predicted molecular activity for the combinations of the highest ranking fragments identified. The user can set a lower activity limit below which no fragments will be reported. As a consequence of the rapid, automated, and objective topomeric CoMFA analysis, significantly more rapid lead optimization of pharmaceutical leads is now possible than was possible in the prior art.

Thus, quite unlike standard CoMFA, topomeric CoMFA provides a method to quickly: 1) identify promising alternative molecular structures; and 2) determine the likely activity of the newly identified structures. Searching of the Virtual Library for fragments having shapes similar to the fragments derived from the activity series may rapidly identify more active molecules based on the initial structure activity relationship data used to generate the topomeric CoMFA model. Of course it is possible, that the fragments identified in the Virtual Library prove to be less active than those used to generate the topomeric CoMFA model. However, that has not proven to be the case to date. The likelihood of discovering more active fragments increases as the number of fragments which can be searched in the Virtual Library increases. Another advantage of using a Virtual Library built along the lines of that described in U.S. Pat. No. 6,240,374 and enhanced with the addition of electrostatic field data required to perform topomeric CoMFA, is that the identification of fragments having similar shape to those fragments derived from the activity series molecules immediately leads to knowledge of synthetic reactions with and without cores in which those fragments can participate. Part of the characterizing data associated with each fragment as taught in U.S. Pat. No. 6,240,374 provides information on synthetic reactions. Thus, use of the topomeric CoMFA methodology with such a Virtual Library, not only leads to predictions of fragments likely to produce molecules having higher activity, but also leads to knowledge of molecules incorporating those fragments which are synthetically accessible. In the real world, what is most desired is a knowledge of molecules having desired characteristics that can be synthesized.

It should be remembered that standard CoMFA has been found to predict molecular activity with a high degree of accuracy. Topomeric CoMFA shares that same heritage. Should the identified fragments predict a higher activity, the previously elusive goal of rapid lead optimization can now be achieved. To perform topomeric CoMFA, it is only necessary to identify the relevant fragments for each molecule in a series and input the activity values. The generation of the topomeric CoMFA model, the searching of the Virtual Library for similar fragment structures, and the calculation of predicted activities for the identified structures can be completed very rapidly by the attached software code.

I. REFERENCES

1. So, Sung-Sau and Karplus, M. (2001) *Evaluation of designed ligands by a multiple screening methods: Application to glycogen phosphorylase inhibitors constructed with a variety of approaches*. J. Comp.-Aid. Mol. Des. 15: 613-647
2. Zhu, L., Hou, T., Chen, L., and Xu, X. (2001) *3D QSAR Analyses of Novel Tyrosine Kinase Inhibitors Based on Parmacophore Alignment*. J. Chem. Inf. Comput. Sci. 41: 1032-1040 (1038)

We claim:

1. A computer implemented method of generating a three-dimensional quantitative structure activity relationship (3D QSAR) of a series of molecules previously identified as having related chemical or biological properties described by a unique parameter value for each molecule in the series comprising the steps of:
    (a) fragmenting the molecules in the series according to a consistent procedure;
    (b) topomerically aligning each fragment according to a defined set of rules;
    (c) calculating steric and electrostatic field descriptor values for the topomerically aligned fragments;
    (d) entering the field descriptor values in a CoMFA table wherein the field descriptors for each fragment are associated with the unique parameter value for the molecule from which the fragment was derived; and
    (e) analyzing the table with the CoMFA methodology wherein the correlation among the molecules in the series is visually displayed.

2. A computer implemented method for predicting the likely activity of a molecule of interest based upon the activities and three dimensional shapes of a series of molecules previously identified as having related chemical or biological properties described by a unique parameter value for each molecule in the series comprising the steps of:
    (a) fragmenting the molecules in the series according to a consistent procedure;
    (b) topomerically aligning each fragment according to a defined set of rules;
    (c) calculating steric and electrostatic field descriptor values for the topomerically aligned fragments;
    (d) entering the field descriptor values in a CoMFA table wherein the field descriptors for each fragment are associated with the unique parameter value for the molecule from which the fragment was derived;
    (e) analyzing the table with the CoMFA methodology to derive a 3D CoMFA QSAR generating coefficients of each field descriptor value in the 3D CoMFA QSAR table;
    (f) fragmenting the molecule of interest according to the same consistent procedure as used to fragment the molecules in the series;
    (g) topomerically aligning each fragment according to the same defined set of rules as used to align the fragments derived from the molecules in the series;
    (h) calculating steric and electrostatic field descriptor values for the topomerically aligned fragments;
    (i) entering the field descriptor values for the fragments derived from the molecule of interest in the 3D CoMFA QSAR table; and
    (j) generating a predicted activity by multiplying the field descriptor values for the fragments derived from the molecule of interest by the associated previously derived 3D CoMFA QSAR coefficients and summing the results
    wherein the activity predicted for the molecule of interest is made available to a user.

3. A computer implemented method of identifying additional molecules which are likely to share the same type of activity as molecules previously identified as sharing the same type of activity, comprising the steps of:
    (a) fragmenting the molecules in the series according to a consistent procedure;
    (b) topomerically aligning each fragment according to a defined set of rules;
    (c) calculating steric and electrostatic field descriptor values for the topomerically aligned fragments;
    (d) entering the field descriptor values in a CoMFA table wherein the field descriptors for each fragment are associated with the unique parameter value for the molecule from which the fragment was derived;
    (e) analyzing the table with the CoMFA methodology to derive a 3D CoMFA QSAR generating coefficients of each field descriptor value in the 3D CoMFA QSAR table;
    (f) using the steric field values of the aligned fragments, searching molecular fragments not derived from the molecules previously identified as sharing the same type of activity, the additional molecular fragments similarly topomerically aligned and characterised by steric and electrosatic field descriptors, to identify those fragments having shapes similar to the fragments used to generate the 3D CoMFA QSAR;

(g) determining the likely activity of molecules formed when fragments identified as being similar in shape are used to replace the fragments generated from the molecules previously identified as sharing the same type of activity by the following steps:
  (1) determining partial activities for each fragment by multiplying the field values for each fragment by the 3D CoMFA QSAR coefficients of the similarly positioned fragment derived from the initial molecules;
  (2) ranking the fragments for each fragment position by partial activity values; and
  (3) combinatorially summing all possible combinations of partial activity values of the fragments, observing fragment position order, to obtain predicted activities for molecules assembled from the identified fragments wherein the structures of molecules assembled from ranked fragments are identified to a user along with their associated predicted activities.

4. A computer implemented method of identifying additional molecules which are likely to share the same type of activity as molecules previously identified as sharing the same type of activity, comprising the steps of:
  (a) fragmenting the molecules in the series according to a consistent procedure;
  (b) topomerically aligning each fragment according to a defined set of rules;
  (c) calculating steric and electrostatic field descriptor values for the topomerically aligned fragments;
  (d) characterising the type and location of features in the topomerically aligned fragments;
  (e) entering the field descriptor values in a CoMFA table wherein the field descriptors for each fragment are associated with the unique parameter value for the molecule from which the fragment was derived;
  (f) analyzing the table with the CoMFA methodology to derive a 3D CoMFA QSAR generating coefficients of each field descriptor value in the 3D CoMFA QSAR table;
  (g) using the steric field values of the aligned fragments, searching molecular fragments not derived from the molecules previously identified as sharing the same type of activity, the additional molecular fragments similarly topomerically aligned and characterised by steric and electrostatic field descriptors and features, to identify those fragments having both shapes and feature types and location similar to the fragments used to generate the 3D CoMFA QSAR;
  (h) determining the likely activity of molecules formed when fragments identified as being similar in shape and features are used to replace the fragments generated from the molecules previously identified as sharing the same type of activity by the following steps:
    (1) determining partial activities for each fragment by multiplying the field values for each fragment by the 3D CoMFA QSAR coefficients of the similarly positioned fragment derived from the initial molecules;
    (2) ranking the fragments for each fragment position by partial activity values; and
    (3) combinatorially summing all possible combinations of partial activity values of the fragments, observing fragment position order, to obtain predicted activities for molecules assembled from the identified fragments wherein the structures of molecules assembled from ranked fragments are identified to a user along with their associated predicted activities.

* * * * *